United States Patent
Zhao

(10) Patent No.: US 10,941,180 B2
(45) Date of Patent: Mar. 9, 2021

(54) PEPTOID COMPOUND, AND DERIVATIVE, SALT, PREPARATION METHOD AND USE THEREOF

(71) Applicant: BOE Technology Group Co., Ltd., Beijing (CN)

(72) Inventor: Zijian Zhao, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 17 days.

(21) Appl. No.: 16/248,263

(22) Filed: Jan. 15, 2019

(65) Prior Publication Data

US 2019/0345198 A1    Nov. 14, 2019

(30) Foreign Application Priority Data

May 11, 2018 (CN) .......................... 20181450473.X

(51) Int. Cl.
| | |
|---|---|
| C07K 7/02 | (2006.01) |
| A61K 49/00 | (2006.01) |
| G01N 33/574 | (2006.01) |
| A61K 47/60 | (2017.01) |
| C07K 7/06 | (2006.01) |
| G01N 33/68 | (2006.01) |

(52) U.S. Cl.
CPC ............ C07K 7/02 (2013.01); A61K 49/0045 (2013.01); G01N 33/57415 (2013.01); A61K 47/60 (2017.08); A61K 49/0056 (2013.01); C07K 7/06 (2013.01); G01N 33/68 (2013.01); G01N 2333/71 (2013.01); G01N 2410/00 (2013.01); Y02P 20/55 (2015.11)

(58) Field of Classification Search
None
See application file for complete search history.

(56) References Cited

U.S. PATENT DOCUMENTS 5,447,916 A * 9/1995 Spellmeyer .......... C07K 5/0202
514/20.6

FOREIGN PATENT DOCUMENTS

WO    WO-2010141421 A1 * 12/2010 ......... G01N 33/6845

* cited by examiner

*Primary Examiner* — James W Rogers
(74) *Attorney, Agent, or Firm* — Westman, Champlin & Koehler, P.A.

(57) ABSTRACT

The present disclosure relates to a peptoid compound, and a derivative, a salt, a preparation method and use thereof. The peptoid compound includes the following subunits: 4-phenylphenethylamine, monoprotected ethylenediamine, monoprotected tetramethylenediamine, 3,4-methylenedioxybenzylamine, isobutylamine, and R(+)-α-methylbenzylamine, in which molecular formulas of the subunits are as follows:

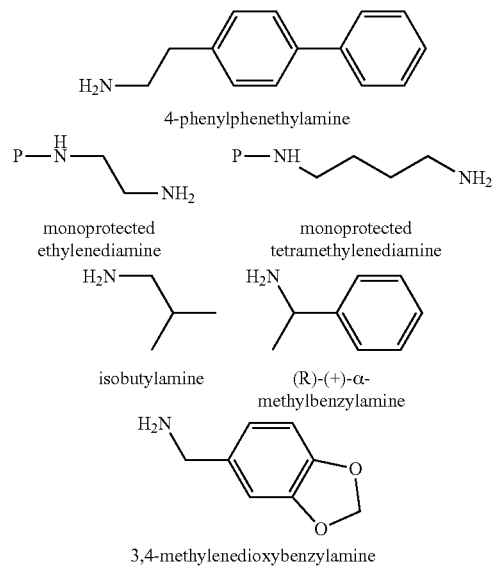

in which P is independently an amino protecting group.

17 Claims, 2 Drawing Sheets

PEPTOID COMPOUND, AND DERIVATIVE, SALT, PREPARATION METHOD AND USE THEREOF

CROSS-REFERENCE TO RELATED APPLICATION

This application claims a priority to Chinese Patent Application No. 201810450473.X filed on May 11, 2018, the disclosures of which are incorporated in their entirety by reference herein.

TECHNICAL FIELD

The present disclosure relates to the field of biomedical technology, in particular to a peptoid compound, a derivative thereof, a salt thereof, a preparation method thereof and use thereof.

BACKGROUND

Breast cancer, a disease associated with human epithelial growth factor receptor 2 (Her2) protein, is one of the most common aggressive malignant tumors in women, accounting for 15% of all female cancers. In recent years, some progress has been made in the early diagnosis and treatment of breast cancer, there are still many unresolved problems.

Circulating tumor cells (CTC) are tumor cells, which are derived from primary tumors or metastatic tumors, achieving the ability to detach from the basement membrane and enter into the tumor cells in the blood vessels through the tissue matrix (epithelial-mesenchymal transition). CTC screening technology is capable of diagnosing cancer in its early development, while providing a good monitoring of cancer development and prognosis. Therefore, the specific recognition of the extracellular region of the Her2 protein on the surface of breast cancer CTC provides a favorable guarantee for capturing the corresponding CTC with high sensitivity. However, the premise of CTC screening is to capture CTC of a very small amount from complex peripheral blood, which has a close inseparable relationship to the probe molecules coupled to the surface of the capture device, effective specific capture may be achieved by affinity combination of the probe molecule and the protein on the surface of the CTC, and thus molecular probes with high affinity and high sensitivity play a crucial role.

A peptoid is a non-naturally folded body similar in structure to the polypeptide and has N-substituted glycine as a unit. It has strong affinity with tumor cells and tissues, and cannot be enzymatically hydrolysed. It is capable of tolerate living samples well, while it has extremely low toxic and side effects. Thus, it may ensure the activity of natural living samples, and is expected to bring a new inspiration for CTC capturing and screening.

SUMMARY

In one aspect, the present disclosure provides a peptoid compound or a salt thereof, the peptoid compound including the following subunits: 4-phenylphenethylamine, monoprotected ethylenediamine, monoprotected tetramethylenediamine, 3,4-methylenedioxybenzylamine, isobutylamine, and R(+)-α-methylbenzylamine, wherein molecular formulas of the subunits are as follows:

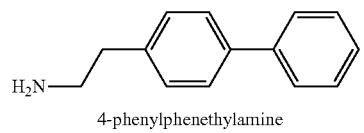
4-phenylphenethylamine

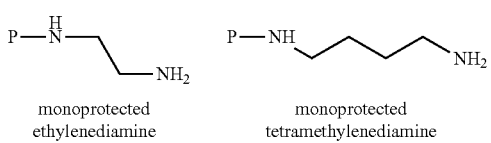
monoprotected ethylenediamine    monoprotected tetramethylenediamine

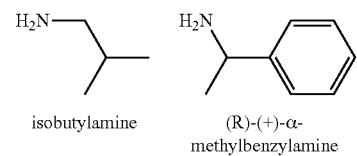
isobutylamine    (R)-(+)-α-methylbenzylamine

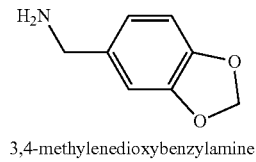
3,4-methylenedioxybenzylamine in which P is independently an amino protecting group.

For example, the order of the subunits included in the peptoid compound is as follows: 4-phenylphenethylamine; monoprotected ethylenediamine; monoprotected tetramethylenediamine; monoprotected tetramethylenediamine; 3,4-methylenedioxybenzylamine; monoprotected tetramethylenediamine; isobutylamine; (R)-(+)-α-methylbenzylamine; and monoprotected tetramethylenediamine.

For example, the peptoid compound has a structure represented by the following Formula I:

Formula I

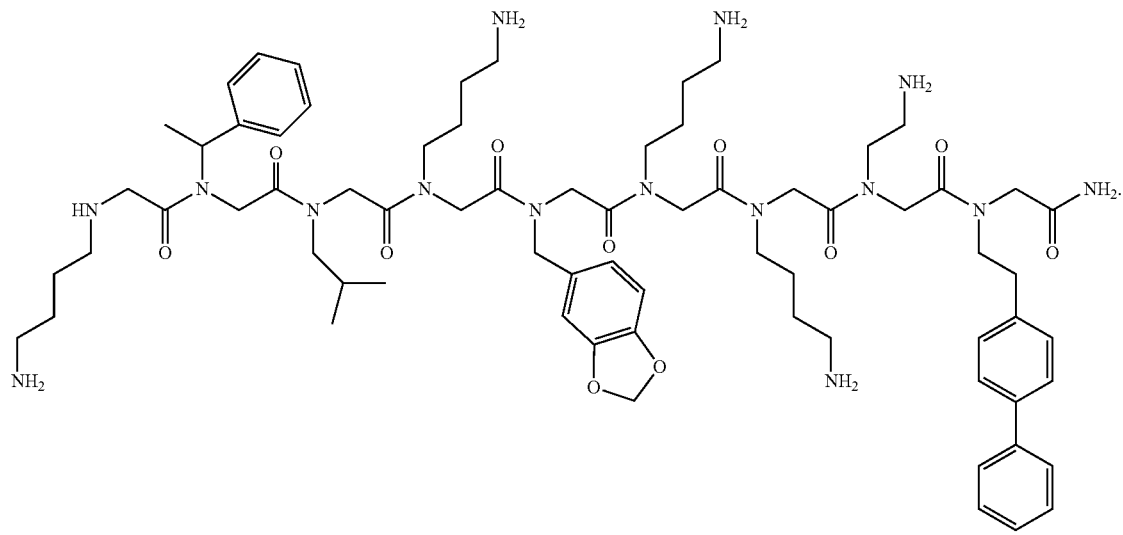

In another aspect, the present disclosure provides a derivative of a peptoid compound, having a structure represented by the following Formula II:

Formula II

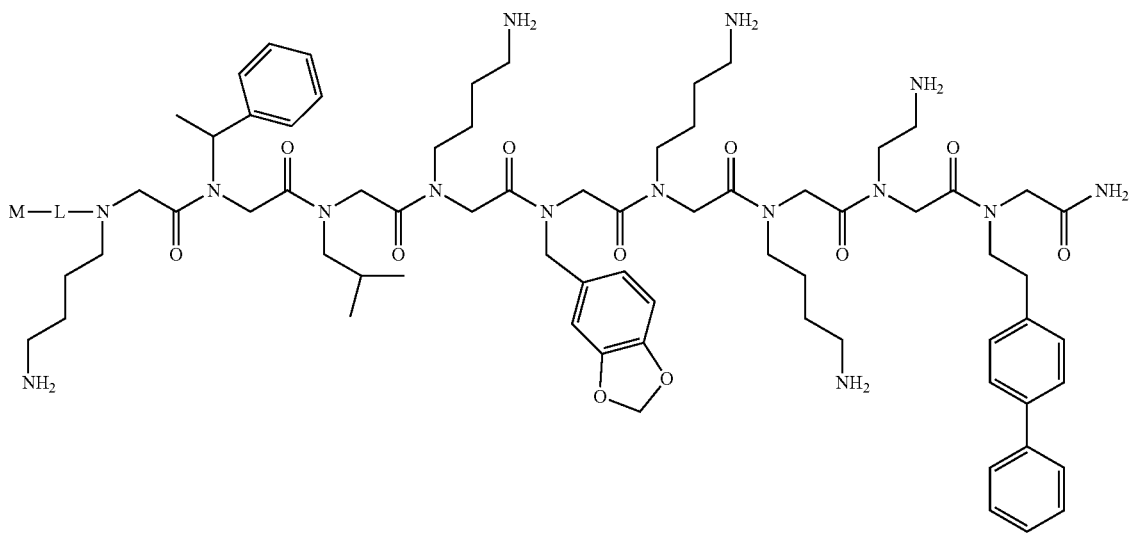

wherein M is a modifying group, and L is absent or is a linking group. In one embodiment, M is a fluorophore, or a group derived from polyethylene glycol, dextran, heparin, polyvinylpyrrolidone, an amino acid or a polysialic acid.

In one embodiment, M is a group derived from polyethylene glycol having a molecular weight of from 100 to 10,000.

In one embodiment, the fluorophore is selected from a group derived from a blue fluorescent dye, a near-infrared fluorescent dye or a green fluorescent dye.

For example, the fluorophore is selected from a coumarin-containing fluorophore, an anthracene-containing fluorophore, a rhodamine fluorophore, a phenanthroimidazole fluorophore, a naphthalene-containing fluorophore, or a group derived from fluorescein isothiocyanate, carboxy fluorescein (FAM), fluorescein thiocyanate (FITC), dansyl chloride, 2,4-dinitrobenzene (Dnp), carbo-xyrhodamine 110, Texas Red, pentamethinecyanine dye (Cy5), or heptamethinecyanine dye (Cy7).

In one embodiment, the linking group is —CO—, —CO(CH$_2$)$_m$—CO—, —NH(CH$_2$)$_m$—CO—, —CONHCO—, —CO(CH$_2$)$_m$—OCO—, —NH(CH$_2$)$_m$—OCO—, —CO(CH$_2$)$_m$—NHCO—, or —NH(CH$_2$)$_m$—NHCO—, wherein each m is independently any integer of from 1 to 10.

For example, the linking group is —CO(CH$_2$)$_2$—CO—.

In an exemplary embodiment, the salt is a salt formed by the peptoid compound with an inorganic or organic acid.

For example, the inorganic acid is hydrochloric acid, sulfuric acid or nitric acid, and the organic acid is acetic acid, sulfonic acid or citric acid.

In another yet aspect, the present disclosure provides a method for preparing the above peptoid compound or the salt thereof, including steps of:

(1) amidating a compound of Formula III with an amino group at an end of a solid phase carrier resin to form an amido bond,

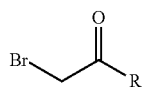

Formula III wherein R is OH or Cl;

(2) adding a subunit to substitute a bromine atom through a nucleophilic substitution reaction to synthesize one subunit;

(3) repeating steps (1) and (2) until all the subunits have been synthesized, in which the subunits are added in an order of: 4-phenylphenethylamine; monoprotected ethylenediamine; monoprotected tetramethylenediamine; monoprotected tetramethylenediamine; 3,4-methylenedioxybenzylamine; monoprotected tetramethylenediamine; isobutylamine; (R)-(+)-α-methylbenzylamine; and monoprotected tetramethylenediamine, molecular formulas of the subunits are as follows:

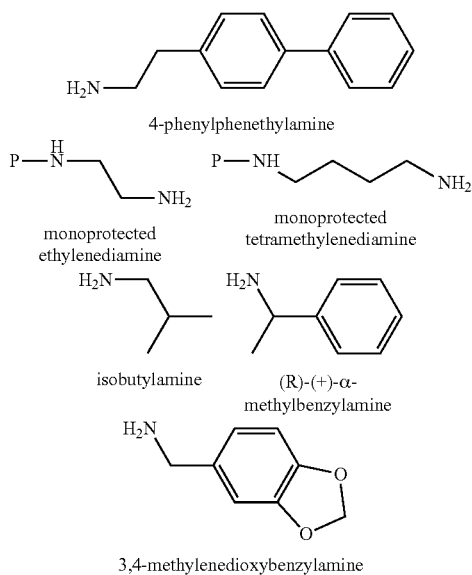

in which P is independently an amino protecting group;

(4) removing an amino protecting group on a side chain, and cleaving the peptoid compound from the resin; and (5) optionally, preparing the peptoid compound obtained in step (4) into a salt thereof.

In another aspect, the present disclosure provides a method for preparing the derivative of the above peptoid compound, including steps of:

(1) amidating a compound of Formula III with an amino group at an end of a solid phase carrier resin to form an amido bond,

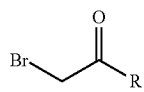

Formula III in which R is OH or Cl;

(2) adding a subunit to substitute a bromine atom through a nucleophilic substitution reaction to synthesize one subunit;

(3) repeating steps (1) and (2) until all the subunits have been synthesized, in which the subunits are added in an order of: 4-phenylphenethylamine; monoprotected ethylenediamine; monoprotected tetramethylenediamine; monoprotected tetramethylenediamine; 3,4-methylenedioxybenzylamine; monoprotected tetramethylenediamine; isobutylamine; (R)-(+)-α-methylbenzylamine; and monoprotected tetramethylenediamine, molecular formulas of subunits are as follows:

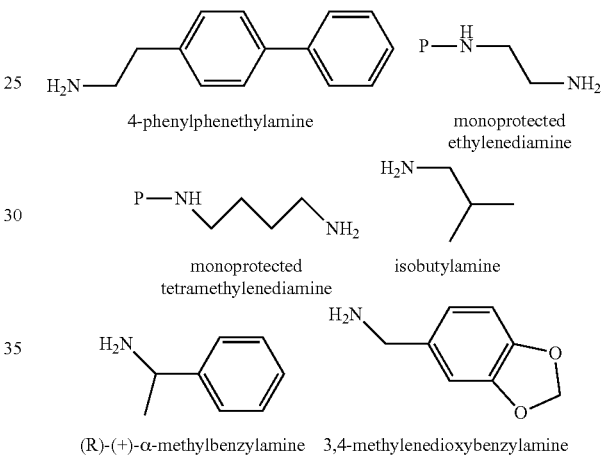

in which P is independently an amino protecting group;

(4') adding a modifier for modification, then removing an amino protecting group on a side chain, and cleaving the peptoid derivative from the resin.

In a further aspect, the present disclosure provides a method for detecting, diagnosing or monitoring a disease associated with Her2 protein using the above peptoid compound or the salt thereof, including: administering the above peptoid compound or the salt thereof to a patient in need thereof.

In one embodiment, the disease associated with the Her2 protein is breast cancer.

In a still another aspect, the present disclosure provides a detecting agent including the above peptoid compound or the salt thereof.

In a still another aspect, the present disclosure provides a detecting agent including the derivative of the above peptoid compound.

In a still another aspect, the present disclosure provides a chip including the above peptoid compound or the salt thereof.

In one embodiment, the chip is a microfluidic chip.

DETAILED DESCRIPTION

Figure 1:
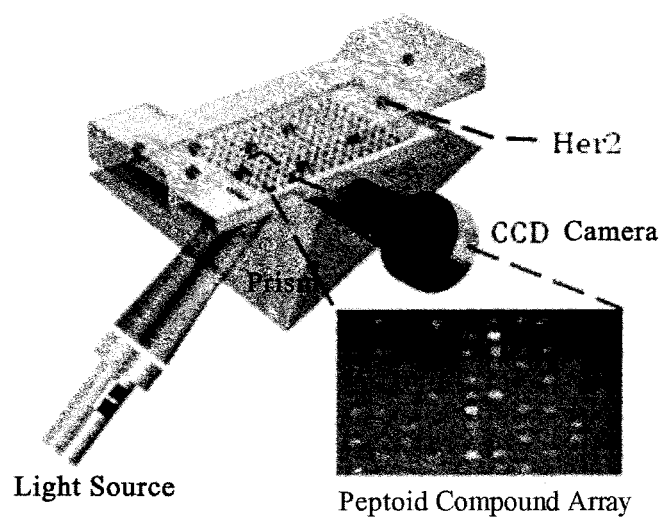
FIG. 1 is a schematic diagram of printing a peptoid compound probe and thereby detecting a serum sample by using surface plasmon resonance imaging (SPRi).

The disclosure will be described in more detail below, but the following detailed description is merely illustrative in nature and is not intended to limit the disclosure. Further, the present invention is not limited to any theory described in the foregoing related art or the disclosure or the following specific embodiments or examples.

In one aspect, the disclosure provides a peptoid compound, having a structure represented by the following Formula I:

Therefore, the present disclosure also provides a derivative of the above peptoid compound, which is a product obtained by modifying the peptoid compound.

The group of the peptoid compound for modifying (hereinafter referred to as a modifying group) is not particularly limited, as long as it is a group known in the art used for modifying a protein, a polypeptide, and a peptoid compound, and may be selected according to actual needs. In some embodiments, M may be a fluorophore, or a group derived from polyethylene glycol (PEG), dextran, heparin, polyvinylpyrrolidone, an amino acid or a polysialic acid.

The molecular weight of the PEG is not particularly limited, as long as the basic function of the peptoid compound may still be achieved after the modification. For example, the molecular weight of PEG may range from 100 to 10,000, such as 150, 200, 300, 400, 500, 800, 1000, 2000, 3000, 4000, and 5000 etc.

The type of the fluorophore is not particularly limited, as long as it may impart a fluorescent property to the peptoid compound after modification and may still achieve the basic function of the peptoid compound. The peptoid compound according to the present disclosure may be modified with Formula I

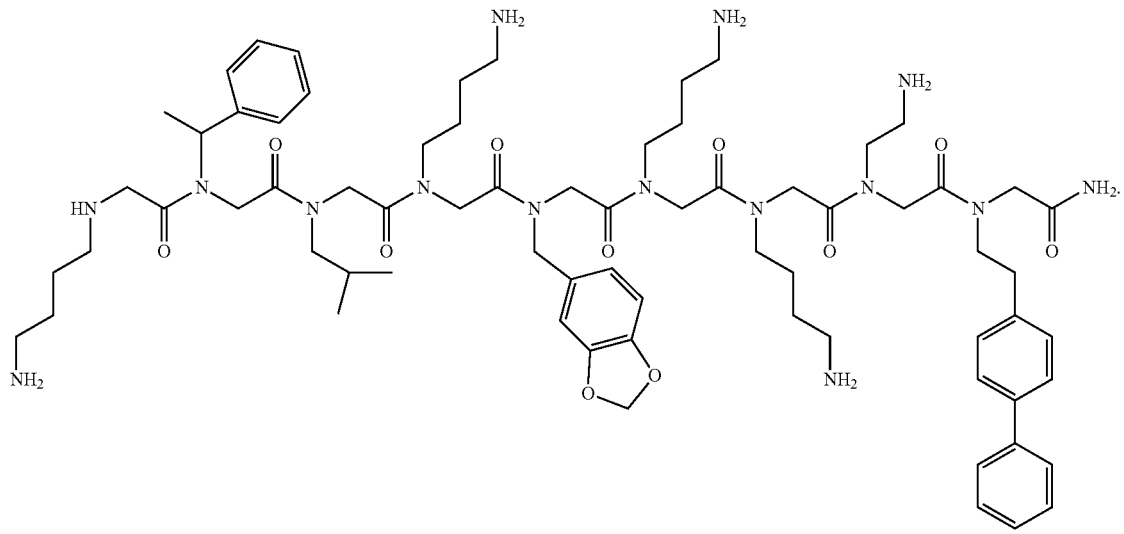

The peptoid compound of the present disclosure may be further modified.

Without being limited to any theory, it is known that drug molecules such as a protein, a polypeptide, and a peptoid compound may have problems such as immunogenicity and toxic side reactions, and short duration of action in vivo, thereby limiting the applications thereof. The above problems may be overcome by partially or completely chemically modifying. Chemical modification may change the properties of the protein, the polypeptide or the peptoid compound molecule, such as eliminating immunogenicity and immunoreactivity, prolonging the duration of action in vivo, improving the efficacy, etc., and thus broadening the range of applications of the protein, the polypeptide or the peptoid compound to a large extent. In addition, after being modified by the fluorophores, drug molecules such as the protein, the polypeptide, and the peptoid compound, may be used to prepare biosensors, for applications such as fluorescence imaging.

one or more fluorophores, e.g., a single fluorescently labeled peptoid compound modified with one fluorophore, or a dual fluorescently labeled peptoid compound labeled with two fluorophores. In some embodiments, the fluorophore may be selected, without limitation, from a group derived from a blue fluorescent dye, a near-infrared fluorescent dye, a green fluorescent dye, or the like, such as a coumarin-containing fluorophore, an anthracene-containing fluorophore, a rhodamine fluorophore, a phenanthroimidazole fluorophore, a naphthalene-containing fluorophore, or a group derived from fluorescein isothiocyanate, carboxy fluorescein (FAM), fluorescein thiocyanate (FITC), dansyl chloride, 2,4-dinitrobenzene (Dnp), carbo-xyrhodamine 110, Texas Red, pentamethinecyanine dye (Cy5), and heptamethinecyanine dye (Cy7).

The method for modifying the peptoid compound is not limited, and methods for modifying a protein, a polypeptide, and a peptoid compound known in the art may be employed as long as the modifying group may be linked to the end of the peptoid compound of the present disclosure. For example, it may be obtained by modifying a peptoid compound synthesized according to the present disclosure, or by simultaneously modifying in the process of synthesizing a peptoid compound according to the present disclosure, and the compound containing the modifying group may react directly with the peptoid compound of the present disclosure, or react with a compound containing the modifying group after being functionalized with the peptoid compound according to the present disclosure, or the compound containing the modifying group and the peptoid compound according to the present disclosure reacted with each other in the presence of a linking compound (for example, succinic acid, glutaric acid, etc.) to form a product having a modifying group-linking group-peptoid compound structure.

In some embodiments, a modifying agent prepared after a compound containing the modifying group is functionalized is reacted with the peptoid compound according to the present disclosure are. The modifying agent may be, for example, polyethylene glycol (PEG) based, fluorescent substance based, dextran based, heparin based, polyvinylpyrrolidone based, polychloro acid based, polysialic acid based modifiers, or the like. Among them, it is optionally the PEG-based modifiers.

Compared with other modifiers, PEG-based modifiers are less toxic, non-antigenic, have good solubility and biocompatibility, and may alter the biodistribution behavior and dissolution behavior of the modified polypeptide. PEG-based modifiers include, but are not limited to, carboxylic acid-based, amide-based, amino acid-based, comb-like, epoxy-based, heterobifunctional PEG modifiers, and the like.

The carboxylic acid-based PEG modifier refers to a PEG modifier obtained by carboxylating a PEG at the terminal, for example, by carboxylating a PEG at the terminal with a diacid or an anhydride thereof. Such PEG modifiers may be, for example, oxalic acid mono PEG ester, malonic acid mono PEG ester, succinic acid mono PEG ester, glutaric acid mono PEG ester, adipic acid mono PEG ester, and the like. The carboxylic acid-based PEG modifiers may be further activated with N-hydroxysuccinimide (NHS).

The amide-based PEG modifier refers to a PEG modifier obtained by further amidating a terminally carboxylated PEG with for example N-hydroxysuccinimide (NHS) Such PEG modifiers may be, for example, PEG succinimide ester (PEG-NHS), PEG succinimide succinate (PEG-SS), PEG succinimide carbonate (PEG-SC), PEG succinimide valerate (PEG-SVA), PEG succinimide glutarate (PEG-SG), PEG succinimide acetate (PEG-SCM), PEG succinimide propionate (PEG-SPA), and the like.

The amino acid-based PEG modifier refers to a PEG modifier obtained by functionalizing a PEG at the terminal with an amino acid. Such PEG modifiers may be, for example, PEG-alanine or the like. The amino acid-based PEG modifier may be further activated with N-hydroxysuccinimide (NHS).

The comb-like-based PEG modifier refers to a PEG modifier prepared by using comb-like-based PEG (or branched PEG).

The epoxy-based PEG modifier refers to a PEG modifier obtained by functionalizing a PEG at the terminal with an epoxy group-containing structure. Such PEG modifiers may be, for example, PEG glycidyl ether.

The heterobifunctional PEG modifier refers to a PEG modifier obtained by functionalizing both ends of PEG with different functional groups. Such PEG modifiers may be, for example, OH-PEG-COOH, OH-PEG-NH$_2$, HCL.NH$_2$—PEG-COOH, maleimide (MAL)-PEG-NHS, and the like.

The molecular weight of the PEG segment in the PEG-based modifier is not particularly limited, as long as the basic function of the peptoid compound may be achieved. For example, the molecular weight of the PEG segment may range from 100 to 10,000, such as 150, 200, 300, 400, 500, 800, 1000, 2000, 3000, 4000, and 5000.

The method for modifying the peptoid compound with a modifying agent is not particularly limited, and various methods disclosed in the related art may be used according to needs.

In one embodiment, the peptoid derivative has the structure as shown in following Formula II:

Formula II

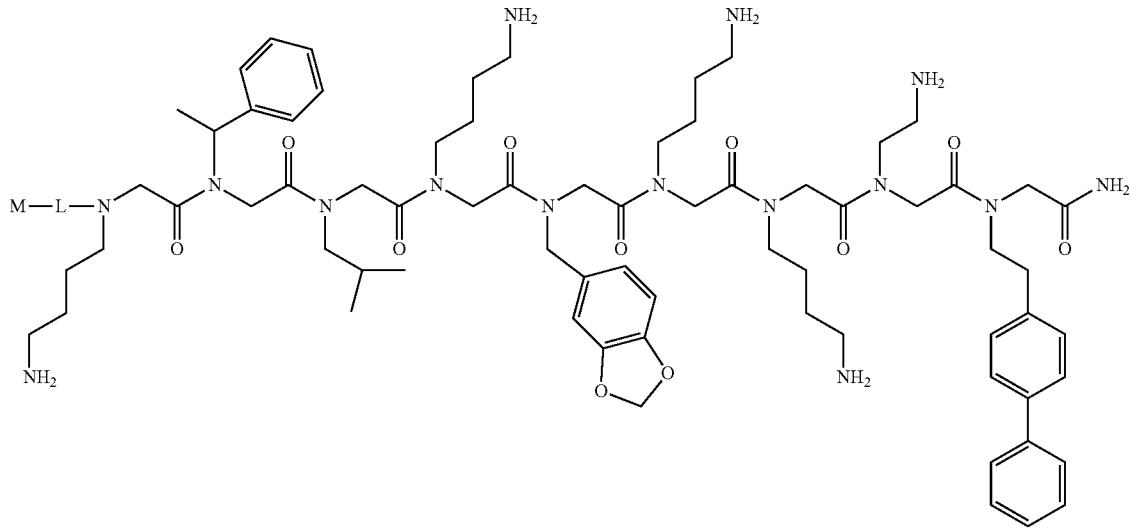

in which M is a modifying group, and L is absent or is a linking group.

The modifying group may be selected without limitation from a fluorophore, or a group derived from polyethylene glycol, dextran, heparin, polyvinylpyrrolidone, an amino acid, a polysialic acid, or the like. In particular, the modifying group may be a group derived from polyethylene glycol. The description of the polyethylene glycol and the fluorophore is the same as the above description.

The linking group is not particularly limited, and is formed by reacting a functional group at the end of the modifying agent with an amino group on the backbone of the peptoid compound. In one embodiment, the linking group may be —CO—, —CO(CH$_2$)$_m$—CO—, —NH(CH$_2$)$_m$—CO—, —CONHCO—, —CO(CH$_2$)$_m$—OCO—, —NH(CH$_2$)$_m$—OCO—, —CO(CH$_2$)$_m$—NHCO—, or —NH(CH$_2$)$_m$—NHCO—, wherein each m is independently any integer of from 1 to 10, e.g., any integer of 1 to 8, 1 to 6, or 1 to 4. Further, the linking group may be —CO(CH$_2$)$_2$—CO—.

The peptoid compound and the derivative thereof of the present disclosure may also be present in the form of a salt. The salt may be, for example, a salt formed by reacting the peptoid compound and the derivative thereof with an inorganic acid, e.g., hydrochloric acid, sulfuric acid, nitric acid or the like; or an organic acid, e.g., acetic acid, sulfonic acid, citric acid or the like, respectively.

The above peptoid compound of the present disclosure may be synthesized according to the subunit sequence of Formula I by a polypeptide synthesis method well known in the art, for example, by a polypeptide solid phase synthesis.

The peptoid derivative of the present disclosure may be obtained by modifying a peptoid compound after synthesizing the above peptoid compound, or by simultaneously modifying in the process of synthesizing the above peptoid compound. The method for performing the modification is described as the above.

The salts of the peptoid compound and the derivative thereof of the present disclosure may be prepared by reacting the peptoid compound and the derivative thereof with an inorganic or organic acid, respectively.

In one embodiment, the method for preparing the peptoid compound, the derivative thereof, or the salt thereof of the present disclosure includes the following steps:

(1) amidating a compound of Formula III with an amino group at an end of a solid phase carrier resin to form an amido bond,

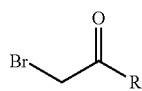

Formula III in which R is OH or Cl;

(2) adding a subunit to substitute a bromine atom through a nucleophilic substitution reaction to synthesize one subunit;

(3) repeating steps (1) and (2) until all the subunits have been synthesized.

in which the subunits are added in the order of: 4-phenylphenethylamine; monoprotected ethylenediamine; monoprotected tetramethylenediamine; monoprotected tetramethylenediamine; 3,4-methylenedioxybenzylamine; monoprotected tetramethylenediamine; isobutylamine; (R)-(+)-α-methylbenzylamine; and monoprotected tetramethylenediamine, (4) removing an amino protecting group on a side chain, and cleaving the peptoid compound from the resin; or (4') adding a modifier for modification, then removing an amino protecting group on a side chain, and cleaving the peptoid derivative from the resin; and (5) optionally, preparing the peptoid compound obtained in step (4) or the peptoid derivative obtained in (4') into a salt thereof.

Molecular formulas of the subunits are as follows:

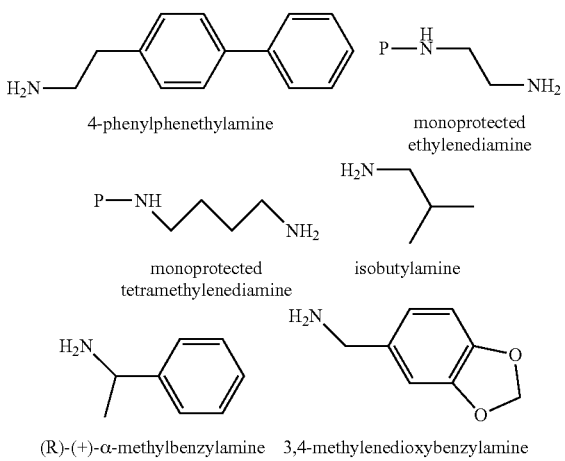

(R)-(+)-α-methylbenzylamine   3,4-methylenedioxybenzylamine in which P is independently an amino protecting group.

As the amino protecting group, an amino protecting group known in the art for the synthesis of a protein, a polypeptide or a peptoid compound may be used without limitation, e.g., amino protecting group listed in *Protective Groups in Organic Synthesis: protection of amino, alkyne hydrogen, and phosphate groups* published by East China University of Science and Technology Press, 2016. In some embodiments, the amino protecting group is 9-fluorenylmethoxycarbonyl (Fmoc) or tert-butoxycarbonyl (Boc).

In the method for preparing the peptoid compound of the present disclosure, an amidation reaction is first performed by amidating a compound of Formula III with an amino group at an end of a solid phase carrier resin to form an amido bond, and then the compound of the Formula III is subjected to an amidation reaction with an amino group of the previous subunit to form an amido bond and a nucleophilic substitution reaction with the latter subunit until all subunits have been synthesized.

The reaction condition of the amidation reaction in the above step (1) is not particularly limited, and may use conventional condition for amidation reaction for synthesizing a protein, a polypeptide or a peptoid compound in the art, as long as the amino group may be acylated and the function of the peptoid compound is not destroyed. For example, the above amidation reaction may be performed in the presence of a condensing agent. The condensing agent may be used without limitation as a condensing agent known in the art for the synthesis of a protein, a polypeptide or a peptoid compound. For example, the condensing agent may be carbodiimide-based condensing agents, e.g., N,N'-diisopropylcarbodiimide (DIC), N,N'-dicyclohexylcarbodiimide (DCC), 1-ethyl-(3-dimethylaminopropyl)carbodiimide (EDC) etc.; benzotriazole-based condensing agents, e.g., 1-hydroxy-benzo-triazole (HOBO; benzenesulfonyl chloride-based condensing agents, e.g., triisopropylbenzenesulfonyl chloride (TPS), etc.; succinimide-based condensing agents, e.g., disuccinimidyl carbonate (DSC), succinimidyl diphenyl phosphate (SDPP), etc.; 2-ethoxy-1-ethoxycarbonyl-1,2-dihydroquinoline (EEDQ); 3-(diethoxyphosphoryloxy)-1,2,3-benzotrizin-4(3H)-one (DEPBT), etc. The amidation reaction may be performed at a temperature of 35 to 40° C. for 10 minutes or more, 20 minutes or more, or 30 minutes or more.

The reaction condition of the nucleophilic substitution reaction in the above step (2) is not particularly limited, and may use conventional condition for nucleophilic substitution reaction for synthesizing a protein, a polypeptide or a peptoid in the art, as long as the bromine atom may be substituted and the function of the peptoid compound is not destroyed. For example, it may be reacted at a temperature of 35 to 40° C. for 30 minutes or more, 60 minutes or more, or 90 minutes or more.

In the above steps (4) and (4'), removing an amino protecting group on a side chain and cleaving the peptoid compound from the resin may be performed simultaneously or sequentially. For example, the peptoid compound is first cleaved from the resin, and then the amino protecting group on the side chain is removed. Alternatively, the amino protecting group on the side chain is first removed, and then the peptoid compound may be cleaved from the resin, or the amino protecting group on the side chain may be removed at the same time that the peptoid compound is cleaved from the resin. The removing the amino protecting group on the side chain and the cleaving the peptoid compound from the resin may employ conventional conditions in the art for performing a protein, a polypeptide or a peptoid compound synthesis, as long as the purpose is achieved and the function of the peptoid compound is not destroyed. In one embodiment, a lysate containing 95% by volume of trifluoroacetic acid, 2.5% by volume of ultrapure water, and 2.5% by volume of triisopropylsilane may be used to remove the amino protecting group on the side chain and cleave the peptoid compound from the resin at the same time.

The description of the modifier in the above step (4') is the same as the above description, and will not be repeated here.

In the above step (5), the method for preparing the peptoid compound obtained in step (4) or the peptoid derivative obtained in step (4') into a salt thereof is not particularly limited, and any salt-forming method known in the art may be employed. For example, the salts of the peptoid compound and the derivative thereof of the present disclosure may be prepared by reacting with acids, e.g., inorganic or organic acids.

In the method for producing the peptoid compound of the present disclosure, a step of purifying the obtained product may also be included according to needs. The method of the purification is not particularly limited, and may use a method for purifying a corresponding similar product known in the art, e.g., precipitation, filtration, dialysis, gel permeation chromatography and the like.

The peptoid compound of the present disclosure, the derivative thereof or the salt thereof may specifically recognize the Her2 protein, and thus it may be used as a molecular probe specifically recognizing the Her2 protein. For example, by coupling to a surface of a chip (e.g., a microfluidic chip), the CTC capture and diagnosis of a disease associated with the Her2 protein (e.g., breast cancer) may be achieved by combining surface plasmon resonance imaging techniques.

In a still another aspect, the present disclosure provides a method for detecting, diagnosing or monitoring a disease associated with Her2 protein using the peptoid compound, the derivative thereof or the salt thereof, including: administering the peptoid compound, the derivative thereof or the salt thereof to a patient in need thereof.

In a yet another aspect, the present disclosure provides a detecting agent including the above peptoid compound, the derivative thereof, and the salt thereof.

The detecting agent may further include: a pharmaceutically acceptable auxiliary materials. In some embodiments, the pharmaceutically acceptable auxiliary materials may include one or more selected from excipients, diluents, carriers, flavoring agents, binders, and fillers.

In a yet still another aspect, the present disclosure provides a method for detecting, diagnosing or monitoring a disease associated with Her2 protein using the above detecting agent, including: administering the above detecting agent to a patient in need thereof.

In one embodiment, the above disease associated with the Her2 protein may be breast cancer.

In one embodiment, the device may be a chip, such as a microfluidic chip.

In a still another aspect, the present disclosure provides a chip including one or more selected from the above peptoid compound, the derivative thereof, and the salt thereof.

In addition to one or more selected from the above peptoid compound, the derivative thereof, and the salt thereof according to the present disclosure, the chip according to the present disclosure may use various blank chips for CTC capture and detection known in the related art and may be prepared according to conventional methods, or may be prepared from commercially available blank chips for CTC capture and detection. In one embodiment, the chip is prepared from a PlexArray HT 3D chip commercially available from Plexera Bioscience, USA.

In the chip of the present disclosure, one or more selected from the above peptoid compound, the derivative thereof and the salt thereof may be coupled to a surface of a chip (for example, a microfluidic chip), and then used for CTC capture and detection. The coupling may be achieved by formulating one or more selected from peptoid compound, the derivative thereof, and the salt thereof according to the present disclosure into a peptoid compound molecular probe sample, and spotting them on the surface of the chip, followed by incubation.

In yet another aspect, the present disclosure provides a method for detecting, diagnosing, or monitoring a disease associated with Her2 protein, the method including using a step of one or more selected from the above peptoid compound, the derivative thereof, and the salt thereof, the above detecting agent or the above step to combine the Her2 protein. In one embodiment, the above disease associated with the Her2 protein may be breast cancer.

The peptoid compound, the derivative thereof or the salt thereof of the present disclosure may be used to detect and monitor the disease associated with the Her2 protein (e.g., breast cancer) by detecting Her2 protein derived from serum in a simpler, more sensitive, lower cost, non-invasive manner, for example, it may be used as a molecular probe coupled to the surface of a chip for CTC capture (e.g., a microfluidic chip).

Advantageous Effect

As compared with the related art, the present disclosure has the following advantageous effects:

(1) The peptoid compound, the derivative thereof and the salt thereof of the present disclosure have strong binding ability to Her2, and the equilibrium dissociation constant KD in the binding kinetic constant between the peptoid compound of the present disclosure and Her2 obtained by the surface plasmon resonance imaging (SPRi) technique is on the order of $10^{-8}$ mole/liter;

(2) The peptoid compound, the derivative thereof and the salt thereof of the present disclosure have high sensitivity to the Her2 protein in the serum, and may be coupled to the surface of the microfluidic chip as an efficient molecular probe to realize CTC capture, and may clearly distinguish the patient from the normal person by detecting the blood signal intensities of the peptoid compound to the patient associated with the Her2 protein and the normal person through surface plasmon resonance imaging technique;

(3) The peptoid compound, the derivative thereof and the salt thereof of the present disclosure may be detected at an early stage of the disease, and do not need to cause trauma to the patient, and have a high detection accuracy and a good specificity;

(4) The peptoid compound of the present disclosure, the derivative thereof and the salt thereof may be synthesized in a simple and low cost manner.

Example

The technical solutions of the present disclosure will be further described by way of examples below. Those skilled in the art should be understood that these examples are only intended to assist in understanding the present disclosure and are not to be considered as a specific limitation to the present disclosure.

To allow those skilled in the art to understand the features and effects of the present disclosure, the following is merely a general description and definition of terms and wording mentioned in the specification and the scope of patent application. Unless otherwise indicated, all technical and scientific terms used herein have the common meaning to those skilled in the art, and in the case of a conflict, the definition of the specification shall prevail.

Unless otherwise indicated, the experimental methods used in the following examples are conventional methods.

Unless otherwise indicated, the materials, the reagents and the like used in the following examples are commercially available.

The SPRi apparatus described in the following examples was Plexera Kx5V2, Plexera Bioscience LLC, USA; and phosphate buffer saline (PBS), phosphoric acid, and proteinase K were prepared according to the product instruction manual. As shown in FIG. 1, the instrument is mainly equipped with a 660 nm LED light source, a CCD image collector and a sensor chip having a microfluidic channel. The instrument displays the change in intensity of the reflected light at each monitoring point over time and records it as surface plasmon resonance (SPR) curve.

Unless otherwise indicated, "Her2 protein" herein refers to the full-length Her2 protein.

Unless otherwise indicated, "patients with breast cancer" herein refers to patients with breast cancer having a high Her2 expression.

Unless otherwise indicated, "M" refers to "mol/L", "μM" refers to "μmol/L", and "mM" refers to "m mol/L".

Preparation Example 1: Preparation of Peptoid Compound

The peptoid compound of the present disclosure was synthesized by a solid phase subunit synthesis, including steps of:

(1) 2 M of bromoacetic acid in N,N-dimethylformamide (DMF) solution (2.5 ml) and 3.2 M of N, N'-diisopropylcarbodiimide (DIC) in DMF solution (2.5 ml) were added into Rink amide AM resin (substitution level of 0.3 mmol/g, 200 mg), and reacted at 37° C. for 30 min to acylate the amino group at the end of the resin;

(2) adding 2 M of the subunit in DMF solution to be added (5 ml), reacting at 37° C. for 90 min to substitute a bromine atom through a nucleophilic substitution reaction to synthesize one subunit;

(3) repeating steps (1) and (2) until the remaining subunits have been synthesized, in which the subunits are added in the order of: 4-phenylphenethylamine; Boc-protected ethylenediamine; Boc-protected tetramethylenediamine; Boc-protected tetramethylenediamine; 3,4-methylenedioxybenzylamine; monoprotected tetramethylenediamine; isobutylamine; (R)-(+)-α-methylbenzylamine; and Boc-protected tetramethylenediamine;

(4) After the synthesis is completed, the amino protecting group on the side chain of the peptoid compound is removed by using a lysate containing 95% by volume of trifluoroacetic acid, 2.5% by volume of ultrapure water and 2.5% by volume of triisopropylsilane, and is cleaved from the resin for use at the same time.

The peptoid compound has a structure represented by the following Formula I:

Formula I

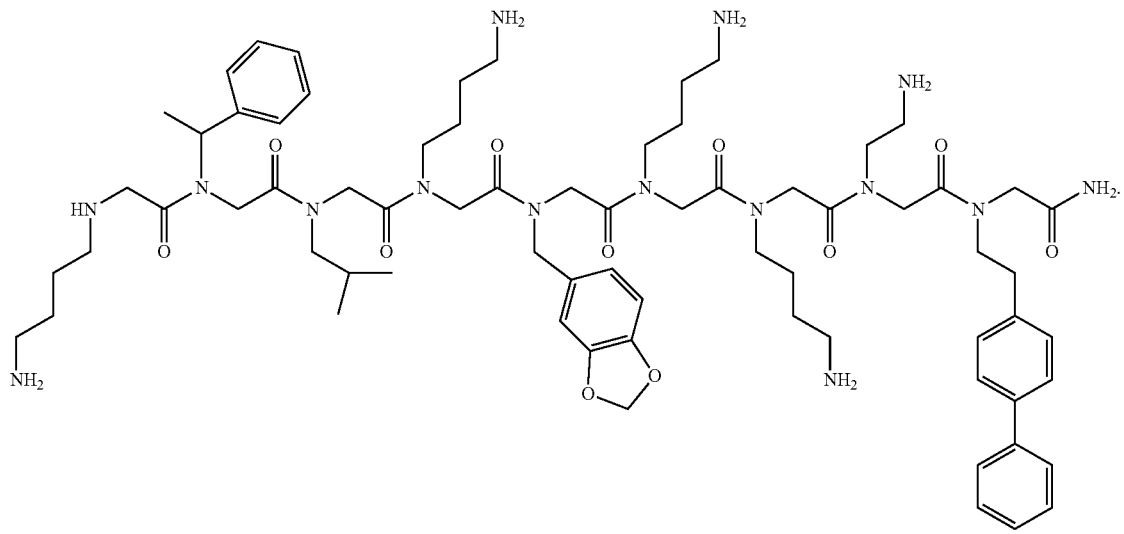

Preparation Example 2: Preparation of the Derivative of the Peptoid Compound (1) Preparation is performed according to steps (1) to (3) of Preparation Example 1;
(2) in 100 ml of deionized water, the monomethoxy-terminated PEG 2000 (10.0 g) and succinic anhydride added in a molar ratio of about 1:5 react with each other, and the reaction was stirred at room temperature overnight to carboxylate the PEG terminal;
(3) 1-(3-dimethylaminopropyl) carbodiimide hydrochloride (EDC, about 0.77 g/10 ml) and N-hydroxysuccinimide (NHS, about 0.115 g/10 ml) were added to the carboxylated PEG in a molar ratio of about 1:1:1, and activated for 1 h;
(4) a peptoid compound not cleaved from the resin prepared in step (1) was added in a molar ratio of about 1:1, and reacted at room temperature for 6 h;
(5) a lysate containing 95% by volume of trifluoroacetic acid, 2.5% by volume of ultrapure water, and 2.5% by volume of triisopropylsilane was added to remove the protecting group on the side chain and to cleave the peptoid derivative from the resin for use.

The resulting peptoid derivative has a structure represented by the following Formula IV:

Formula IV

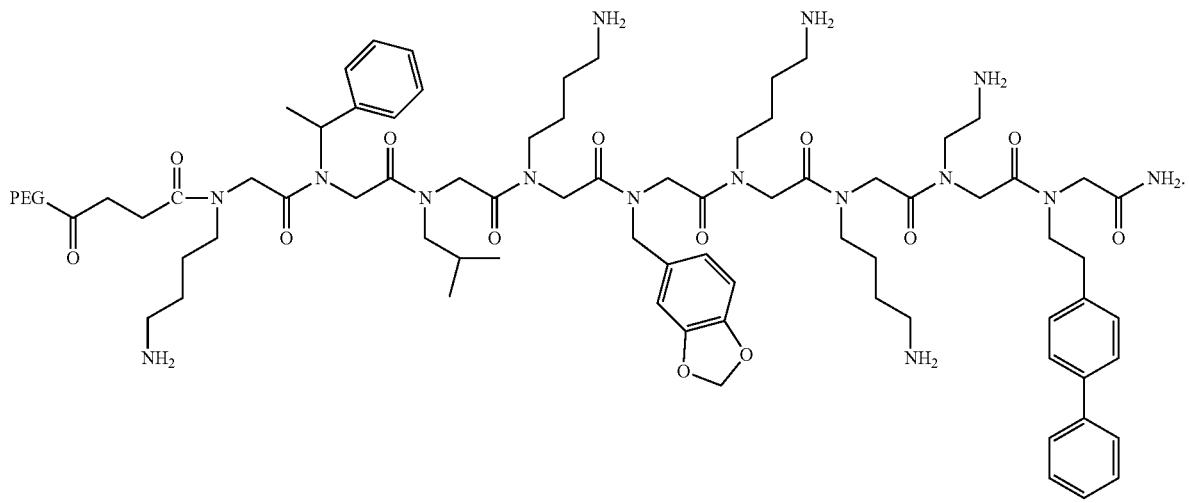

Experimental Example 1: Binding Ability of the Peptoid Compound to Her2 Protein

The specific steps for testing the binding ability of the peptoid compound of Preparation Example 1 or the peptoid Derivative of Preparation Example 2 to the Her2 protein by surface plasmon resonance imaging techniques are shown as follows:

(1) dissolving the peptoid compound of Preparation Example 1 or the peptoid derivative of Preparation Example 2 into ddH$_2$O at a concentration of 1 to 1000 µM to prepare a peptoid compound molecular probe sample to be spotted at a gradient concentration of 1-1000 µM;

(2) spotting the above peptoid compound molecular probe sample on a surface of a 3D chip (PlexArray HT, Plexera Bioscience, USA), in which each sample is repeated for 3 points, incubated at 4° C. for 12 hours, and washed by 10×PBS, 1×PBS and ultrapure water in sequence. The chip was then blocked with 1 M of aminoethanol hydrochloride for 30 minutes, then washed 5 times with ultrapure water, and finally dried with clean nitrogen;

(3) mounting the chip on the SPRi instrument, measuring SPRi angle and adjusting it to the optimal optical position, in which relevant detection points including sample points and blank points are selected in the detection area, and the experimental flow rate is set to 2 µL/s;

(4) selecting PBS as a buffer solution, flowing it into a flow cell until the baseline is stable, and sequentially passing through Her2 (purchased from Sigma (USA)) solutions at concentrations of 2.632 µM, 1.316 µM, 0.658 µM, and 0.329 µM (for the peptoid derivatives of Preparation Example 2, concentrations of Her2 are 0.50 µM, 0.25 µM, 0.125 µM, and 0.0625 µM) for detection, in which the binding time was 300 seconds and the dissociation time was 300 seconds, and phosphoric acid was regenerated between each concentration.

Figure 2:
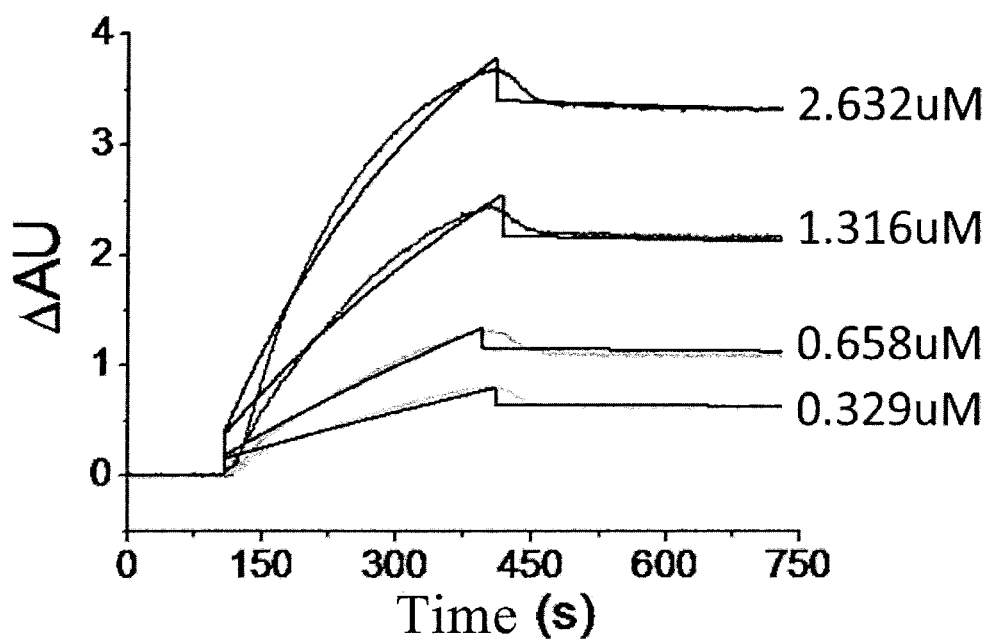
FIG. 2 is a graph showing the results of an affinity test of the interaction between the peptoid compound molecule and the Her2 protein according to Experimental Example 1.
Figure 4:
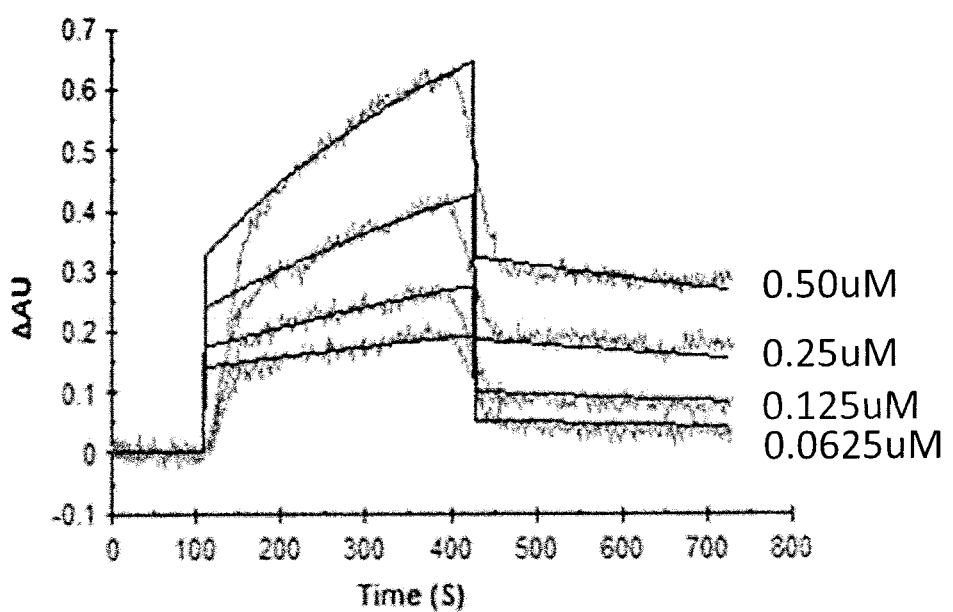
FIG. 4 is a graph showing the results of an affinity test of the interaction between the peptoid derivative molecule and the Her2 protein according to Experimental Example 2.

The detection results are shown in FIGS. 2 and 4, in which the abscissa is time in seconds (s), and the unit of the ordinate ΔAU is arbitrary unit, which refers to value obtained by subtracting the baseline signal of the initial PBS buffer from the combined signal after passing the mobile phase through the array, indicating the intensity of the binding signal. Each concentration in the figure corresponds to two lines, in which the relatively tortuous and light-colored lines are the test results of the PlexArray HT test, and the relatively straight and darker lines are the lines obtained by fitting BIAevalution 4.1. After fitting, the equilibrium dissociation constant KD of the peptoid compound of Preparation Example 1 was 6.18×10$^{-8}$ mol/L, and the equilibrium dissociation constant KD of the peptoid derivative of Preparation Example 2 was 6.07×10$^{-8}$ mol/Lol/L. This result indicates that the peptoid compound or the derivative thereof according to the present disclosure has a strong binding ability to Her2 and has a strong affinity for Her2.

Experimental Example 2: Detection of Serum Signals by Peptoid Compound

The specific steps for testing the detection of the peptoid compound of Preparation Example 1 or the peptoid Derivative of Preparation Example 2 for the blood of the patients with breast cancer by surface plasmon resonance imaging techniques are shown as follows:

(1) in the same manner as in Experimental Example 1, preparing the same 3D chip as in Experimental Example 1, mounting the chip on the SPRi instrument, measuring SPRi angle and adjusting it to the optimal optical position, in which relevant detection points including sample points and blank points are selected in the detection area, and the experimental flow rate is set to 2 µL/s;

(2) After selecting PBS as the buffer solution and flowing it into a flow cell until the baseline is stable, and introducing the serum of the patient with breast cancer and the normal person (diluted 1:5000 in volume), in which the binding time was 300 seconds and the dissociation time was 300 seconds, and each sample is regenerated by introducing phosphoric acid and proteinase K therebetween.

Figure 3:
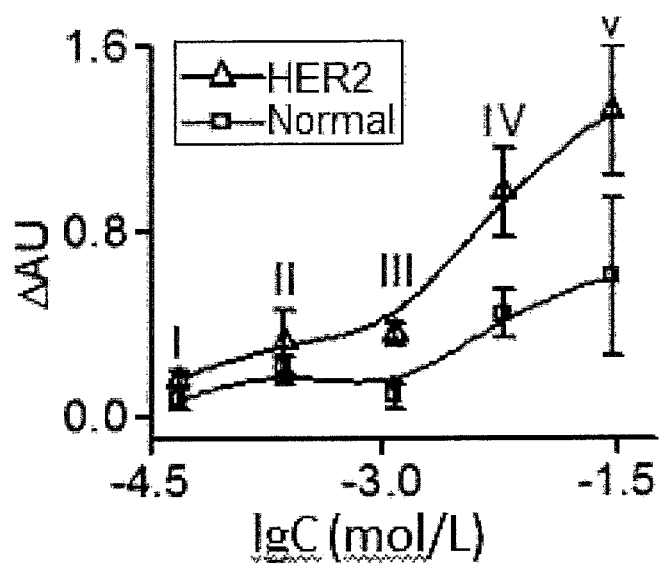
FIG. 3 is a graph showing the result of detecting serum samples from a normal subject and from a breast cancer patient by using different peptoid compound concentrations, thereby screening and distinguishing a patient and a normal subject, wherein C represents a concentration.

The results of the test are shown in FIG. 3, in which the meaning of ΔAU is the same as in FIGS. 2 and 4, and the peptoid compound concentrations corresponding to I, II, III, IV and V are: 80 µM, 400 µM, 2 mM, 10 mM, 50 mM, respectively. As can be seen from the results in FIG. 3, with the increase of the concentration of the peptoid compound, the peptoid compound probe may clearly distinguish the serum samples of the patients with breast cancer. Therefore, the peptoid compound of the present disclosure have high sensitivity to the Her2 protein in the serum, and may be coupled to the surface of the microfluidic chip as an efficient molecular probe to realize CTC capture, and may clearly distinguish the patient from the normal person by detecting the blood signal intensities of the peptoid compound to the patient associated with the Her2 protein and the normal person through surface plasmon resonance imaging technique.

In summary, the peptoid compound and the derivative thereof of the present disclosure are peptoid compound having high sensitivity to Her2 protein and providing a new choice for diagnosing and monitoring breast cancer.

The Applicant claims that the present disclosure describes the process of the present disclosure by the above examples, but the present disclosure is not limited to the above process steps, that is, it does not mean that the implement of the present disclosure must rely on the above process steps. Those skilled in the art that should understand that any modifications to the present disclosure, equivalent substitutions of the materials used for the present disclosure and the addition of the auxiliary components, the selection of the specific manners, and the like, are all fall in the protection scope and the disclosure scope of the present disclosure.

What is claimed is:

1. A peptoid compound or a salt thereof, wherein the peptoid compound is produced from the following subunits: 4-phenylphenethylamine, monoprotected ethylenediamine, monoprotected tetramethylenediamine, 3,4-methylenedioxybenzylamine, isobutylamine, and R(+)-α-methylbenzylamine, wherein molecular formulas of the subunits are as follows:

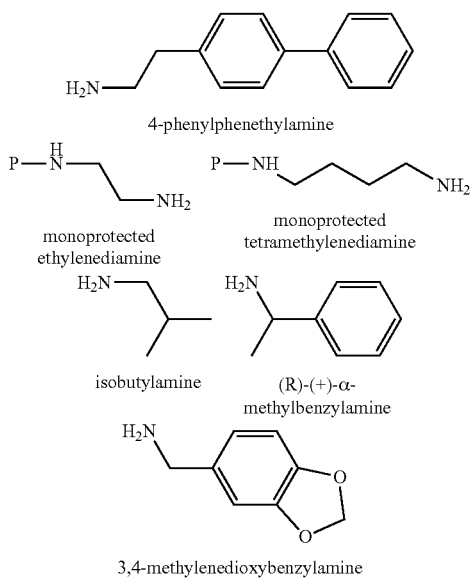

in which P is independently an amino protecting group; wherein the peptoid compound has a structure represented by the following formula I:

Formula I

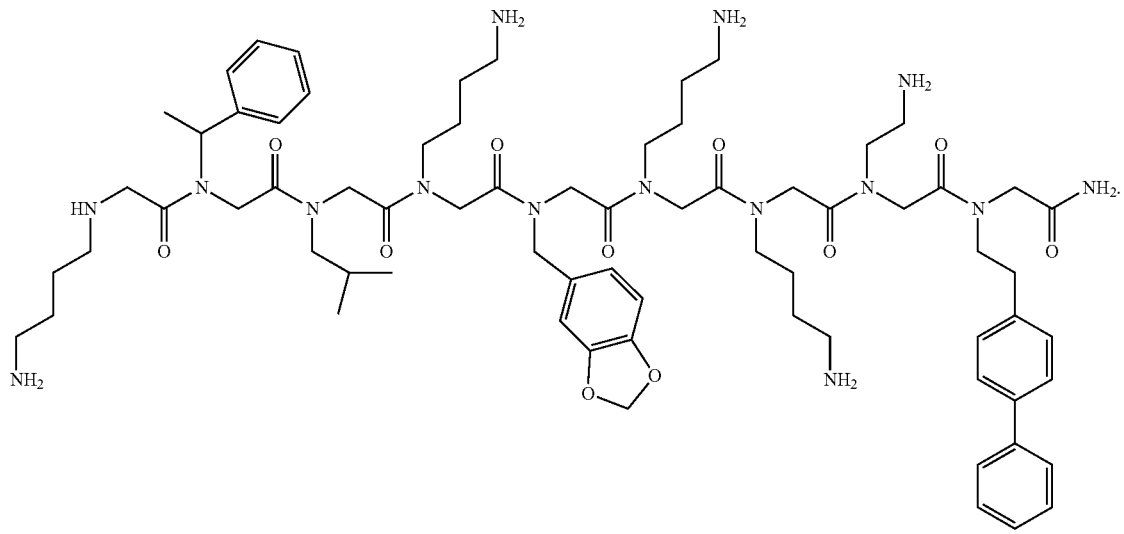

2. A derivative of a peptoid compound, having a structure represented by the following Formula II:

Formula II

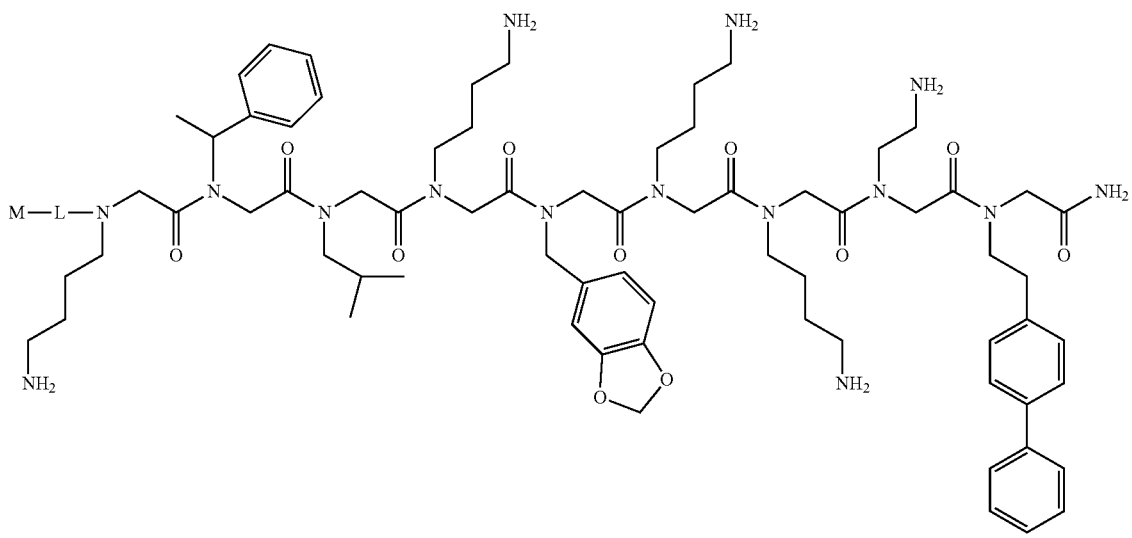

wherein M is a modifying group, and L is absent or is a linking group.

3. The derivative of the peptoid compound of claim 2, wherein M is a fluorophore, or a group derived from polyethylene glycol, dextran, heparin, polyvinylpyrrolidone, an amino acid or a polysialic acid.

4. The derivative of the peptoid compound of claim 2, wherein M is a group derived from polyethylene glycol having a molecular weight of from 100 to 10,000.

5. The derivative of the peptoid compound of claim 3, wherein the fluorophore is selected from a group derived from a blue fluorescent dye, a near-infrared fluorescent dye or a green fluorescent dye.

6. The derivative of the peptoid compound of claim 3, wherein the fluorophore is selected from a coumarin-containing fluorophore, an anthracene-containing fluorophore, a rhodamine fluorophore, a phenanthroimidazole fluorophore, a naphthalene-containing fluorophore, or a group derived from fluorescein isothiocyanate, carboxy fluorescein (FAM), fluorescein thiocyanate (FITC), dansyl chloride, 2,4-dinitrobenzene (Dnp), carbo-xyrhodamine 110, Texas Red, pentamethinecyanine dye (Cy5), or heptamethinecyanine dye (Cy7).

7. The derivative of the peptoid compound of claim 2, wherein the linking group is —CO—, —CO(CH$_2$)$_m$—CO—, —NH(CH$_2$)$_m$—O—, —CONHCO—, —CO(CH$_2$)$_m$—OCO—, —NH(CH$_2$)$_m$—OCO—, —CO(CH$_2$)$_m$—NHCO—, or —NH(CH$_2$)$_m$—NHCO—, wherein each m is independently any integer of from 1 to 10.

8. The derivative of the peptoid compound of claim 2, wherein the linking group is —CO(CH$_2$)$_2$—CO—.

9. The peptoid compound or the salt thereof of claim 1, wherein the salt is a salt formed by the peptoid compound with an inorganic or organic acid.

10. The peptoid compound or the salt thereof of claim 1, wherein the inorganic acid is hydrochloric acid, sulfuric acid or nitric acid, and the organic acid is acetic acid, sulfonic acid or citric acid.

11. A method for producing the peptoid compound or the salt thereof of claim 1, comprising steps of:
(1) amidating a compound of Formula III with an amino group at an end of a solid phase carrier resin to form an amido bond,

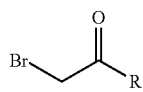

Formula III wherein R is OH or Cl;
(2) adding a subunit to substitute a bromine atom through a nucleophilic substitution reaction to synthesize one subunit;
(3) repeating steps (1) and (2) until the following subunits have been synthesized

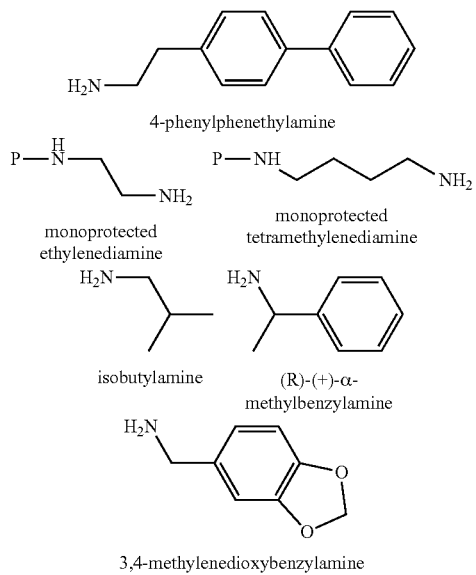

wherein P is independently an amino protecting group;
wherein the subunits are added in an order of: 4-phenylphenethylamine; monoprotected ethylenediamine; monoprotected tetramethylenediamine; monoprotected tetramethylenediamine; 3,4-methylenedioxybenzylamine; monoprotected tetramethylenediamine; isobutylamine; (R)-(+)-α-methylbenzylamine; and monoprotected tetramethylenediamine,
(4) removing an amino protecting group on a side chain, and cleaving the peptoid compound from the resin; and
(5) optionally, preparing the peptoid compound obtained in step (4) into a salt thereof.

12. A method for producing the derivative of the peptoid compound of claim 2, comprising steps of:

(1) amidating a compound of Formula III with an amino group at an end of a solid phase carrier resin to form an amido bond,

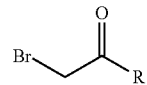

Formula III wherein R is OH or Cl;
(2) adding a subunit to substitute a bromine atom through a nucleophilic substitution reaction to synthesize one subunit;
(3) repeating steps (1) and (2) until the following subunits have been synthesized,

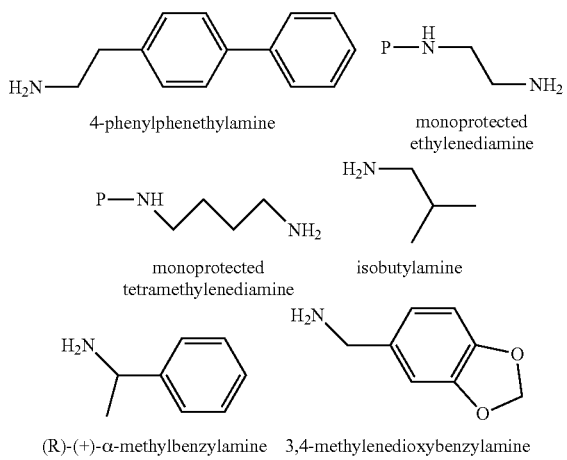

wherein P is independently an amino protecting group; and
wherein the subunits are added in an order of: 4-phenylphenethylamine; monoprotected ethylenediamine; monoprotected tetramethylenediamine; monoprotected tetramethylenediamine; 3,4-methylenedioxybenzylamine; monoprotected tetramethylenediamine; isobutylamine; (R)-(+)-α-methylbenzylamine; and monoprotected tetramethylenediamine,
(4') adding a modifier for modification, then removing an amino protecting group on a side chain, and cleaving the peptoid derivative from the resin.

13. A method for detecting, diagnosing or monitoring a disease associated with Her2 protein using the peptoid compound or the salt thereof of claim 1, comprising:
administering the peptoid compound or the salt thereof of claim 1 to a patient in need thereof.

14. The method of claim 13, wherein the disease associated with Her2 protein is breast cancer.

15. A detecting agent, comprising the peptoid compound or the salt thereof of claim 1.

16. A detecting agent, comprising the derivative of the peptoid compound of claim 2.

17. A microfluidic chip, comprising the peptoid compound or the salt thereof of claim 1.

* * * * *

UNITED STATES PATENT AND TRADEMARK OFFICE
CERTIFICATE OF CORRECTION

PATENT NO. : 10,941,180 B2
APPLICATION NO. : 16/248263
DATED : March 9, 2021
INVENTOR(S) : Zijian Zhao Page 1 of 1

It is certified that error appears in the above-identified patent and that said Letters Patent is hereby corrected as shown below:

On the Title Page

Foreign Application Priority Data item (30), Line 1, please insert the correct CN priority number of --201810450473.X-- and delete the incorrect priority number of "20181450473.X".

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*